US010537376B2

(12) United States Patent
Hagg

(10) Patent No.: US 10,537,376 B2
(45) Date of Patent: Jan. 21, 2020

(54) HIGH-FREQUENCY SURGICAL DEVICE

(71) Applicant: ERBE ELEKTROMEDIZIN GMBH, Tuebingen (DE)

(72) Inventor: Martin Hagg, Wannweil (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 314 days.

(21) Appl. No.: 14/409,386

(22) PCT Filed: May 23, 2013

(86) PCT No.: PCT/EP2013/060560
§ 371 (c)(1),
(2) Date: Dec. 18, 2014

(87) PCT Pub. No.: WO2013/189684
PCT Pub. Date: Dec. 27, 2013

(65) Prior Publication Data
US 2015/0320477 A1 Nov. 12, 2015

(30) Foreign Application Priority Data

Jun. 18, 2012 (EP) ..................................... 12172428

(51) Int. Cl.
*A61B 18/12* (2006.01)
*A61B 18/00* (2006.01)
(52) U.S. Cl.
CPC ....... *A61B 18/1206* (2013.01); *A61B 2018/00607* (2013.01); *A61B 2018/128* (2013.01)
(58) Field of Classification Search
CPC ............ A61B 18/1206; A61B 18/1233; A61B 2018/00589; A61B 2018/00601;
(Continued)

(56) References Cited

U.S. PATENT DOCUMENTS 3,478,744 A 11/1969 Leiter
4,473,075 A 9/1984 Rexroth
(Continued)

FOREIGN PATENT DOCUMENTS

DE 10 2008 004 241 A1 7/2009
EP 0 194 078 A2 9/1986
(Continued)

OTHER PUBLICATIONS

J. Eggleston et al., "Electrosurgical Devices." The Biomedical Engineering Handbook, Second Edition, 2 Volume Set, Dec. 28, 1999.

*Primary Examiner* — Jaymi E Della
*Assistant Examiner* — Sean W Collins
(74) *Attorney, Agent, or Firm* — Blank Rome LLP

(57) ABSTRACT

A high-frequency surgical device having a high-frequency generator, which produces a high-frequency output signal for treating, in particular for cutting or coagulating, biological tissue, the high-frequency generator being designed in such a way that the output signal of the high-frequency generator has a predetermined fundamental frequency and a modulation apparatus being provided, which is used to modulate the output signal with a modulation frequency, the modulation frequency being smaller than the fundamental frequency. The high-frequency surgical device is characterized in that the modulation frequency is at least 100 kHz, and in that the output signal can be modulated in such a way that a crest factor of the modulated output signal suitable for a specific application of the high-frequency surgical device arises.

13 Claims, 2 Drawing Sheets

(58) Field of Classification Search
CPC ........... A61B 2018/00607; A61B 2018/00726; A61B 2018/00732; A61B 2018/128
See application file for complete search history.

(56) References Cited

U.S. PATENT DOCUMENTS

| | | | |
|---|---|---|---|
| 4,658,820 A | | 4/1987 | Klicek |
| 5,472,443 A | * | 12/1995 | Cordis ................... A61B 18/12 606/32 |
| 6,939,347 B2 | * | 9/2005 | Thompson ......... A61B 18/1206 128/898 |
| 2006/0155270 A1 | * | 7/2006 | Hancock ................ A61B 18/18 606/33 |
| 2007/0066971 A1 | * | 3/2007 | Podhajsky ......... A61B 18/1206 606/34 |
| 2008/0039832 A1 | | 2/2008 | Palanker et al. |
| 2011/0071518 A1 | | 3/2011 | Gilbert |
| 2012/0203217 A1 | * | 8/2012 | Brannan ............ A61B 18/1815 606/33 |
| 2013/0035679 A1 | * | 2/2013 | Orszulak ............ A61B 18/1445 606/33 |

FOREIGN PATENT DOCUMENTS

| | | |
|---|---|---|
| EP | 1 197 184 A1 | 4/2002 |
| JP | S61-222441 A | 10/1986 |
| JP | H11-19092 A | 1/1999 |
| JP | 2000-342599 A | 12/2000 |
| WO | WO 96/14021 A1 | 5/1996 |

* cited by examiner

HIGH-FREQUENCY SURGICAL DEVICE

TECHNICAL FIELD

Embodiments of the invention relate to a high-frequency surgical device (HF surgical device).

BACKGROUND

An HF surgical device are generally well-known, for example, from DE 10 2008 004 241 A1. FIG. 6 of this application shows a basic diagram of a known HF surgical device 1 according to DE 10 2008 004 241 A1. It comprises an HF generator 3 which produces a high-frequency output signal a, in particular a high-frequency alternating current, which is supplied to an HF surgical instrument electrically connected to the HF generator 3. The HF surgical instrument may, for example, be an instrument for argon plasma coagulation or for HF cutting which acts by means of one or a plurality of active electrodes on a patient's biological tissue 5 that is to be treated. The patient's tissue 5 to be treated acts in this case as a load impedance which is variable according to treatment level. The HF surgical device 1 further comprises a power supply unit 7 which converts the line voltage (50 Hz AC) into a voltage suitable for the HF generator.

Normally, the high frequency power is initially generated in the HF generator 3 with a carrier or fundamental frequency and is amplified in downstream amplifier stages. Depending on the application, the output signal having the fundamental frequency that is produced by the HF generator 3 is modulated over time, in particular with a variable duty cycle. To do this, it is possible either to act directly on the HF generator 3 using a modulation apparatus 9 in such a manner that the output signal is modulated by pulsing or scanning the high frequency power, i.e. by correspondingly switching the output signal on and off. This is therefore pulse-width modulation (PWM), the pulse frequency or switching frequency determining the modulation depth of the output signal. The modulation frequency $f_{Modulation}$ results in this case from the following formula:

$$f_{Modulation} = 1/T,$$

where T is the cycle duration of the square wave modulation signal. For this, the HF generator may have, for example, a circuit arrangement with MOSFET transistors which are switched on and off alternately. In this case, the modulation apparatus 9 is usually activated by a control device 11.

Another known possibility of modulating the output signal is direct activation of the power supply unit 7 by means of the control device 11. As a result of this, it becomes possible to modulate the amplitude of the output signal of the HF generator 3, the control device 11 acting as the modulation apparatus 9.

The fundamental frequency of the HF generator is normally around 300 to 500 kHz. Modulation normally takes place with frequencies between 1 kHz and 50 kHz. Preferably, however, modulation frequencies greater than 20 kHz are used to prevent the generation of unpleasant noises. However, with "pulsed argon plasma coagulation", for example, lower modulation frequencies in the Hz range can also be used.

It is generally specified for HF surgical devices that low-frequency current fractions which may flow via the patient and consequently may trigger neuromuscular stimulation (e.g. muscle twitching) must be limited to very low values. If this specification is met, certain parts of the application may be designated as CF (cardiac floating). One drawback of these conventional low modulation frequencies is that they are below the limit above which, according to current scientific knowledge, neuromuscular phenomena, such as muscle twitching, no longer occur. It has been ascertained that this limit is approx. 100 kHz. A relevant standard, IEC 60601-2-2, therefore rules that the fundamental frequency of HF surgical devices must be greater than 200 kHz. It is overlooked here, however, that the low modulation frequencies must be taken into account even with a fundamental frequency greater than 200 kHz because they are clearly visible in the frequency spectrum of the overall output signal and may therefore induce neuromuscular phenomena.

Although it is known from the prior art to provide so-called decoupling capacitors in the patient circuit to avoid neuromuscular stimulation due to low-frequency and thus neuromuscularly effective modulation signals, said decoupling capacitors are unable to completely prevent neuromuscular stimulation which is induced in particular by the interaction of sparks between the active electrode of the surgical instrument and the tissue.

SUMMARY

An object of embodiments of the present invention is, therefore, to create an HF surgical device which safely prevents the occurrence of neuromuscular phenomena.

The high-frequency surgical device that achieves this object comprises a high-frequency generator, which produces a high-frequency output signal for treating, in particular for cutting or coagulating, biological tissue, the high-frequency generator being designed in such a way that the output signal of the high-frequency generator has a predetermined fundamental frequency, and a modulation apparatus being provided, which is used to modulate the output signal with a modulation frequency, the modulation frequency being smaller than the fundamental frequency. The high-frequency surgical device is characterized in that the modulation frequency is at least 100 kHz, and in that the output signal can be modulated in such a way that a crest factor of the modulated output signal suitable for a specific application of the high-frequency surgical device arises.

An essential point of embodiments of the invention is, therefore, that neuromuscular phenomena can be ruled out in that the modulation frequency does not fall below 100 kHz. It must be noted, however, that the frequency band gap between the modulation frequency and the fundamental frequency of the HF generator must not be too small since otherwise it will not be possible to set a large enough crest factor for a specific application of the HF surgical device, the crest factor describing the ratio of the peak amplitude of the output signal to its effective value. If, therefore, the modulation depth of the output signal and the fundamental frequency are not adapted to each other in a suitable manner, it is no longer possible to achieve the aim of a higher peak voltage with a low effective voltage, i.e. a higher crest factor. The crest factor is particularly important in HF surgery as it can mathematically describe the modulation depth of the HF generator's output signal. Different modulation depths and therefore crest factors of the output signal must be implemented depending on the HF generator's area of use. For instance, to obtain a suitable coagulation level for tissue coagulation of, for example, CF=2.5, the modulation depth of the HF generator's output current must consequently be set accordingly. Thus, according to embodiments of the invention, the fundamental frequency of the HF generator and the modulation depth of the output signal are adapted to each other in such a way that a suitable crest factor results, i.e. a crest factor sufficiently large for a specific application, on condition that the modulation frequency does not fall below 100 kHz. The fundamental frequency of the output signal and the modulation frequency are adapted to each other in such a way that crest factors ranging from 1.5 to 15, in particular ranging from 2 to 14, 3 to 13, 4 to 12, 5 to 11, 6 to 10, 7 to 9 or ranging from 1.5 to 14, 1.5 to 13, 1.5 to 12, . . . , 1.5 to 3 or 1.5 to 2 respectively can be adjusted. To be able to achieve the intended effects, crest factors between 1.4 (for unmodulated pure sinusoidal signals, such as are used during cutting or non-sparking contact coagulation) and 15 (for non-contact spray coagulation for example) or even larger are usually required.

In one embodiment of the invention, the output signal is modulated by means of pulse width modulation. It may also be provided that the modulation frequency and the fundamental frequency are constant. In another embodiment of the invention, on the other hand, it may be provided that the modulation frequency is variable while the fundamental frequency is constant for modification of the crest factor. It may be further provided that a suitable crest factor is adjustable by varying the duty cycle of the modulation signal. This is particularly advantageous if the modulation frequency is kept constant. The invention preferably enables the adjustment of crest factors of the output signal (a) ranging from 1.5 to 15.

The crest factor is preferably determined based on the output signal and should preferably not fall below a predetermined minimum value. A corresponding recording device which records the modulation frequency, the generator's fundamental frequency and the crest factor may be provided.

Consequently, at a specified desired modulation frequency, which is greater than 100 kHz, modulation of the fundamental frequency is adjusted to the modulation frequency such that a predetermined crest factor to be set is achieved. For example, a crest factor can be adjusted for effective contact coagulation and/or for non-contact coagulation with low cutting effect. It is clear, therefore, that the crest factor can vary depending on the actual use of the surgical device, for example for cutting and/or coagulating tissue or a similar HF surgical treatment.

A high frequency generator in which the modulation frequency is equal to or greater than 200 kHz is especially preferred. The value of the fundamental frequency must accordingly be greater, in particular significantly greater than 500 kHz. It is particularly advantageous if the fundamental frequency is greater than five times the modulation frequency. In particular, according to embodiments of the invention, the fundamental frequencies may be in the single-digit or even multi-digit megahertz range.

A method for operating a high-frequency surgical device is additionally proposed for achieving the object referred to above. The method is characterised in that the fundamental frequency is modulated with a modulation frequency of at least 100 kHz and that the output signal is modulated in such a way that a crest factor of the modulated output signal suitable for a specific application of the high-frequency surgical device arises.

DETAILED DESCRIPTION

Figure 1:
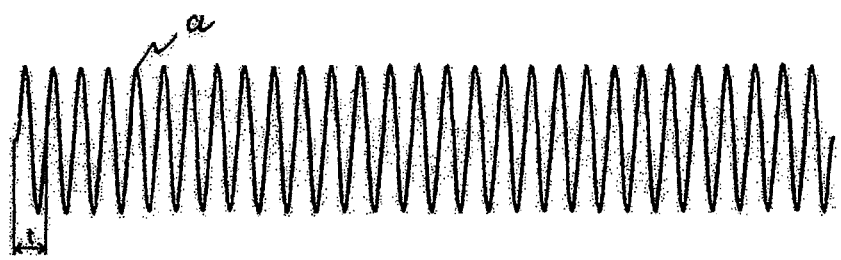
FIG. 1 is a schematic representation of an output signal of an HF generator in the form of a continuous sinusoidal voltage.

FIG. 1 shows an output signal a with a generator frequency $f_{Generator}$ which results from the following formula:

$$f_{Generator}=1/t,$$

where t is the cycle duration of the output signal a and where the output signal a is presented as the output voltage in the present case. The output signal a of an HF generator 3 shown in FIG. 1 is presented in its original form, i.e. unmodulated. The continuous sinusoidal signal according to FIG. 1 has, by way of example, a crest factor of CF=1.41.

Figure 2:
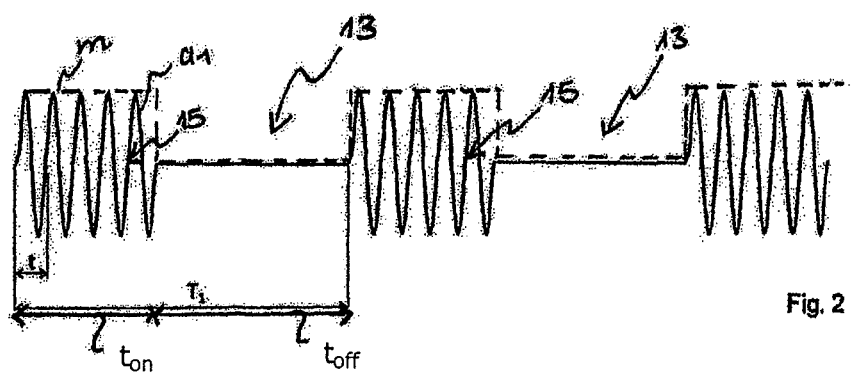
FIG. 2 a schematic representation of a modulated output signal with a crest factor modified compared to the unmodulated output signal.
Figure 3:
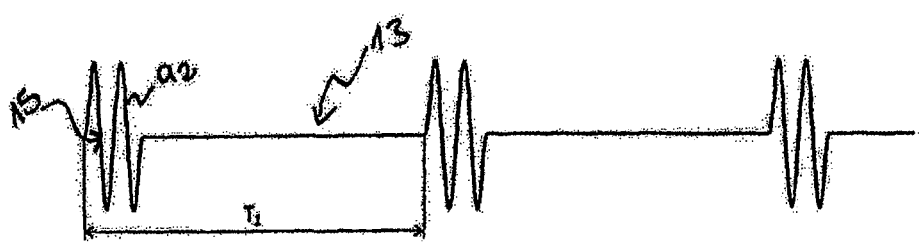
FIG. 3 a schematic representation of a modulated output signal of the HF generator with a crest factor even further modified compared to the unmodulated output signal.
Figure 4:
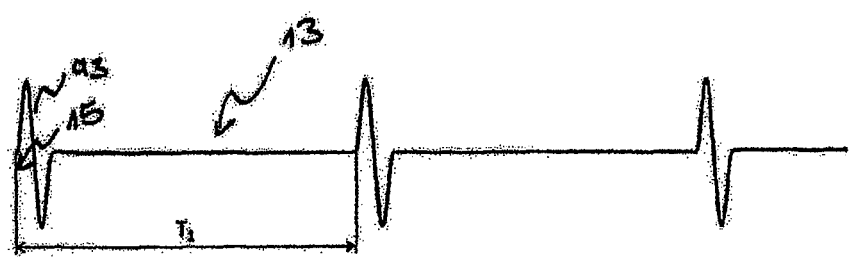
FIG. 4 a schematic representation of a modulated output signal of the HF generator with a crest factor even further modified compared to the unmodulated output signal.

FIGS. 2 to 4 show schematic representations of modulated output signals a1, a2 and a3, in which the fundamental frequency of an HF generator 3 $f_{Generator}$ is constant and matches the fundamental frequency shown in FIG. 1. Unlike the output signal a shown in FIG. 1, output signals a1, a2 and a3 from FIGS. 2 to 4 are modulated, however, by a corresponding modulation apparatus 9 and a corresponding modulation signal m. The modulation form chosen here is a pulse-width modulation which is brought about by means of the square wave modulation signal m. The square wave modulation signal m has an on time $t_{on}$ and an off time $t_{off}$ which together result in the cycle duration $T_1$ of the modulation signal. Pulse pauses 13 and pulse packets 15 which are separated from each other by the pulse pauses arise due to the on and off times of the output signal a1. The modulation frequency, which can be calculated according to the formula below, arises in turn from the cycle duration $T_1$ of the modulation signal m:

$$f_{Modulation}=1/T_1.$$

What is referred to as the duty cycle D can be determined from the ratio of the on time to the sum of the on and off time of the modulation signal m:

$$D=t_{on}/(t_{on}+t_{off})=t_{on}/T_1.$$

FIG. 2 shows a pulse-width-modulated output signal a1. In other words, the output signal a1 was modulated by a square wave pulse which has a cycle duration $T_1$ that was chosen in such a way according to embodiments of the invention that the resulting modulation frequency is $f_{Modulation}=1/T_1 \geq 100$ kHz. It becomes clear that the crest factor CF of the output signal a1 of the HF generator 3 shown in FIG. 2 is larger than the crest factor of the unmodulated output signal a shown in FIG. 1, as the pulse pauses 13 between the pulse packets 15 ensure a reduction in the effective value of the output signal a1. Consequently, the crest factor which results from the ratio of the peak value, i.e. the maximum amplitude, to the effective value of the output signal becomes larger on reducing the effective value of the output signal a1.

FIG. 3 shows a schematic representation of another modulated output signal a2 which has a modified pulse width modulation such that an increased crest factor CF results compared to FIGS. 1 and 2. As in FIG. 2, the fundamental frequency of the generator $f_{Generator}$ is also unchanged with output signal a2 according to FIG. 3 and, according to embodiments of the invention, the modulation frequency $f_{Modulation}$ is also chosen to be greater than or equal to 100 kHz and corresponds to the modulation frequency shown in FIG. 2 which is apparent in the corresponding cycle durations $T_1$.

Increasing the crest factor CF is achieved with the output signal a2 according to FIG. 3 by varying the duty cycle D while the modulation frequency $f_{Modulation}$ remains constant at 100 kHz. At the same time, FIG. 3 makes it clear that the pulse pauses 13 between the pulse packets 15 are greater than in the example according to FIG. 2. This is achieved by reducing the on time $t_{on}$ while reducing the off time $t_{off}$ of the square wave pulse m. As a result of this increase in the pulse pause 13 between the pulse packets 15, there is a reduction in the effective value of the output signal a2 such that the crest factor CF is increased. In other words, the number of cycles t per pulse packet 15 is decreased due to the increase in the pulse pause 13.

FIG. 4 shows yet another example for a modulated output signal a3 of the HF generator 3 that has a crest factor CF which is increased even further compared to FIGS. 1 to 3. As was also the case in FIGS. 2 and 3, the fundamental frequency $f_{Generator}$ of the HF generator 3 was not modified which manifests itself in the constant cycle duration t of the output signal in the pulse packets 15. Accordingly, the modulation frequency $f_{Modulation}$ was also not modified compared to the modulations shown in FIGS. 2 and 3 which the constant cycle duration $T_1$ also shows. Nevertheless, the modulated output signal a3 shown in FIG. 4 has a crest factor CF which is increased even further compared to FIGS. 2 and 3.

Further increasing the crest factor is achieved by increasing the pulse pauses 13 between the pulse packets 15 even further while the cycle durations t per pulse packet 15 are further decreased. In FIG. 4, a pulse packet 15 has only a cycle t of the output signal a3. As a result, the effective value of the output signal a3 is deceased in turn such that the crest factor CF becomes even larger compared to the examples shown in FIGS. 2 and 3.

Thus, a modification of the duty cycle D also takes place in FIGS. 3 and 4 by means of pulse width modulation in such a way that, with a fixed fundamental frequency $f_{Generator}$ of the HF generator 3 and with a fixed modulation frequency $f_{Modulation}$, the crest factor can be adapted to a wide range of applications, such as HF coagulation or an HF cutting procedure.

Overall, it can thus be noted that with constant fundamental frequency $f_{Generator}$ and constant modulation frequency $f_{Modulation}$, the crest factor can be increased by reducing the duty cycle D of the modulation signal. To do this, it is necessary to select the fundamental frequency and the modulation frequency in such a manner that crest factors can be adjusted by pulse-width modulation within a sufficiently large range, preferably from 1.5 to 15. This requires a relatively large gap between the fundamental frequency $f_{Generator}$ and the modulation frequency $f_{Modulation}$, where the boundary condition $f_{Modulation} \geq 100$ kHz must be met in order to safely prevent neuromuscular stimulation. To meet the requirements referred to above, the fundamental frequency preferably amounts to five times the modulation frequency.

Figure 5:
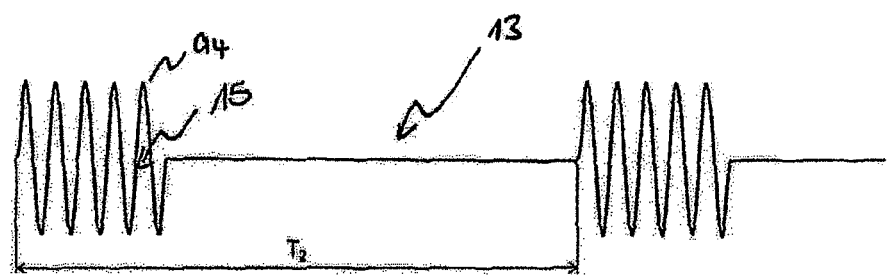
FIG. 5 a schematic representation of a modulated output signal of the HF generator with a crest factor modified compared to the unmodulated output signal.
Figure 6:
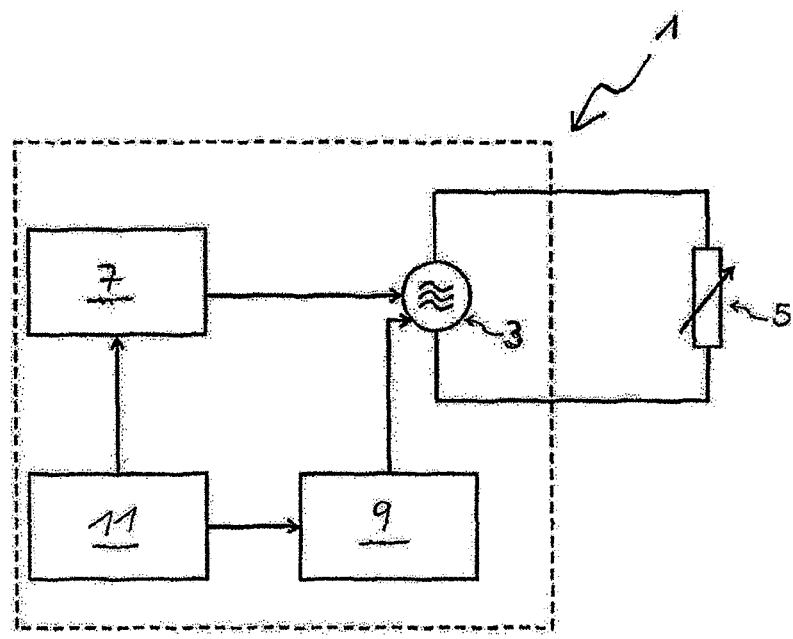
FIG. 6 a schematic representation of an HF surgical device known from the prior art, for example, from DE 10 2008 004 241 A1. The reference numbers of FIG. 6 are also used to explain a high-frequency surgical device according to embodiments of the invention.

FIG. 5 shows another embodiment of the invention in which the fundamental frequency $f_{Generator}$ of the output signal a4 is unchanged while an increase in the crest factor CF is produced by reducing the modulation frequency $f_{Modulation}$, as distinguished from the variation shown in FIGS. 2-4. According to this, the cycle duration $T_2$ of the modulation signal according to FIG. 5 is greater than the cycle duration $T_1$ used in FIG. 2, while the cycles t of the pulse packets 15 match in the embodiments of FIGS. 2 and 5. However, instead of keeping the modulation frequency $f_{Modulation}$ constant, as shown in FIGS. 2 to 4, and merely reducing the cycles t per pulse packet 15 or increasing the pulse pauses 13, in FIG. 5 only the pulse pause 13 was increased without decreasing or increasing the number of cycles per pulse packet 15. It is therefore shown that the crest factor can also be increased by decreasing the modulation frequency $f_{Modulation}$.

However, it is also necessary in this embodiment of the invention for the boundary condition $f_{Modulation} = 100$ kHz to be met in order to safely prevent neuromuscular stimulation. Therefore, with this embodiment too there must also be a sufficiently large gap between the fundamental frequency of the generator and the modulation frequency to be able to implement crest factors within a sufficiently large range, preferably from 1.5 to 15, by varying the modulation frequency in the range $\geq 100$ kHz.

Overall, FIGS. 2 to 5 show that the fundamental frequency of the generator must be increased by several times compared to the modulation frequency to be able to generate appropriately large and variable crest factors, particularly within the range from 1.5 to 15, for a wide range of applications. For example, it may be sufficient for a cutting procedure using an HF surgical instrument if the output signal has been modulated in such a manner that it has a crest factor of 1.5. For a coagulation procedure, on the other hand, larger crest factors, particularly within the range of approx. 2.5, should be present. In addition, it is possible to implement various mixed forms of cutting and coagulation procedures using an HF surgical device for which, in turn, other crest factors, particularly within the range between 1.5 and 2.5, should be present. Moreover, there are applications, e.g. non-contact spray coagulation, for which crest factors of 15 or even larger are required to achieve the desired treatment effect.

It is crucial for embodiments of the present invention that not only the fundamental frequency of the generator is greater than 100 kHz, that is to say, it lies in particular within a range between 300 to 600 kHz, but also that the modulation frequency $f_{Modulation}$ does not fall below 100 kHz. The crest factor which should be adjusted for a specific application of the HF surgical device 1 must then be adjusted via a suitable modulation method, on condition that the modulation frequency does not fall below 100 kHz. As mentioned, for this it is necessary for the fundamental frequency of the generator 3 to exceed the modulation frequency by several times. In particular, according to embodiments of the invention, the fundamental frequencies may be in the single-digit or even multi-digit megahertz range.

Overall, therefore, it can be seen that embodiments of the present invention safely prevents the occurrence of neuromuscular stimulation in that the modulation frequency is at least 100 kHz and consequently lies above the limit above which, according to current scientific knowledge, neuromuscular phenomena, such as muscle twitching, no longer occur.

At the same time, a suitable crest factor for a specific application, such as contact coagulation or a cutting procedure is achieved in that the fundamental frequency is significantly higher than the usual 350 kHz. As a result, an adequate gap is created between the frequency bands of the modulation frequency and the fundamental frequency, which permits the production of a sufficiently large crest factor that is in particular larger than 15.

The invention claimed is:

1. A high-frequency surgical device having a high-frequency generator that produces a high-frequency output signal for treating, in particular for cutting or coagulating, biological tissue, the high-frequency generator being configured such that the output signal of the high-frequency generator has a predetermined fundamental frequency and further configured to form a closed electric circuit with the biological tissue; the high-frequency generator comprising a modulation apparatus used to modulate the output signal with a modulation frequency, the modulation frequency being smaller than the fundamental frequency,
wherein the modulation frequency is at least 100 kHz, and the output signal can be modulated such that a crest factor of the modulated output signal is adjustable within a range between 5 and 15, and
wherein the high-frequency generator is configured such that the modulation frequency and the crest factor of the modulated output signal control sparks between an active electrode and the biological tissue to provide a coagulation mode with reduced neuromuscular stimulation.

2. The high-frequency surgical device of claim 1, wherein the output signal is modulated by means of pulse width modulation.

3. The high-frequency surgical device of claim 1, wherein the modulation frequency and the fundamental frequency are constant.

4. The high-frequency surgical device of claim 1, wherein the modulation frequency is variable and the fundamental frequency is constant.

5. The high-frequency surgical device of claim 1, wherein the crest factor is adjustable by varying a duty cycle of the modulation frequency.

6. The high-frequency surgical device of claim 1, wherein the modulation frequency is greater than 200 kHz.

7. The high-frequency surgical device of claim 1, wherein the fundamental frequency is greater than five times the modulation frequency.

8. A method for operating a high-frequency surgical device having a high-frequency generator for producing a high-frequency output signal with a fundamental frequency for treating, in particular for cutting or coagulating, biological tissue, the method comprising:
forming a closed electric circuit between the high-frequency generator and the biological tissue;
modulating the output signal with a modulation frequency which is smaller than the fundamental frequency such that a crest factor of the modulated output signal is adjustable within a range between 5 and 15; and
modulating the fundamental frequency with a modulation frequency of at least 100 kHz; and
controlling sparks between an active electrode and the biological tissue to provide a coagulation mode with reduced neuromuscular stimulation as a result of the modulation frequency and the crest factor of the modulated output signal.

9. The method of claim 8, wherein modulating the output signal is by means of pulse width modulation.

10. The method of claim 8, further comprising:
adjusting the crest factor by varying a duty cycle of the modulation signal at a constant modulation frequency and constant fundamental frequency.

11. The method of claim 8, further comprising:
varying the modulation frequency to generate the crest factor.

12. The method of claim 8, wherein the modulation frequency is greater than 200 kHz.

13. The method of claim 8, wherein the fundamental frequency is greater than five times the modulation frequency.

* * * * *